(12) United States Patent
Wheatley

(10) Patent No.: US 9,668,645 B2
(45) Date of Patent: Jun. 6, 2017

(54) IMAGING PROBES AND ASSOCIATED DEVICES, SYSTEMS, AND METHODS UTILIZING ELECTROSTATIC ACTUATORS

(71) Applicant: Novartis AG, Basel (CH)

(72) Inventor: Barry Lynn Wheatley, Oceanside, CA (US)

(73) Assignee: NOVARTIS AG (CH)

( * ) Notice: Subject to any disclaimer, the term of this patent is extended or adjusted under 35 U.S.C. 154(b) by 491 days.

(21) Appl. No.: 14/274,074

(22) Filed: May 9, 2014

(65) Prior Publication Data

US 2015/0320307 A1    Nov. 12, 2015

(51) Int. Cl.
*A61B 3/14*        (2006.01)
*A61B 3/10*        (2006.01)
*A61B 3/00*        (2006.01)

(52) U.S. Cl.
CPC .............. *A61B 3/10* (2013.01); *A61B 3/0008* (2013.01); *A61B 3/102* (2013.01)

(58) Field of Classification Search
CPC ......... A61B 3/10; A61B 3/0008; A61B 3/102; A61B 5/0066; A61B 5/0084; A61B 5/6852; A61B 5/0062; A61B 5/0035; A61B 1/00172; A61B 1/002; A61B 1/00165; A61B 8/12; A61B 8/445; A61B 8/4461; A61B 18/24; A61B 18/14; G02B 23/2423; G02B 6/262; G02B 6/357; G02B 2006/0098; G02B 21/0028; G02B 21/0036; G02B 26/103
USPC ................ 351/206, 246; 600/425, 459, 462; 359/201.1
See application file for complete search history.

(56) References Cited

U.S. PATENT DOCUMENTS

| | | | |
|---|---|---|---|
| 6,485,413 B1 | 11/2002 | Boppart et al. | |
| 8,496,579 B2 | 7/2013 | Koenig et al. | |
| 2004/0151466 A1* | 8/2004 | Crossman-Bosworth | G02B 6/25 385/140 |
| 2004/0254474 A1 | 12/2004 | Seibel et al. | |
| 2008/0177138 A1 | 7/2008 | Courtney et al. | |
| 2008/0243002 A1* | 10/2008 | Munce | A61B 5/0062 600/459 |
| 2009/0028407 A1 | 1/2009 | Seibel et al. | |
| 2010/0125239 A1 | 5/2010 | Perry et al. | |
| 2013/0012811 A1 | 1/2013 | Schmitt et al. | |

(Continued)

FOREIGN PATENT DOCUMENTS

DE    102006046554 A1    4/2008

*Primary Examiner* — Bumsuk Won
*Assistant Examiner* — Collin X Beatty

(57) ABSTRACT

Devices, systems, and methods that utilize at least one charged electrode to impart motion to an optical fiber positioned within an imaging probe by an electrostatic force are provided. In some embodiments, an ophthalmic imaging probe can include a handle; a cannula coupled to the handle; an optical fiber positioned at least partially within the handle and the cannula, the optical fiber configured to receive an imaging light from an imaging light source and guide the imaging light to an optical element positioned within the cannula; and an actuator system configured to impart motion to the optical fiber, the actuator system including an electrode positioned within the cannula and configured to impart motion to the optical fiber by selectively imparting an electric charge to the electrode and/or the electrically conductive layer of the optical fiber.

20 Claims, 5 Drawing Sheets

(56) References Cited

U.S. PATENT DOCUMENTS

2013/0158392 A1\* 6/2013 Papac .................... A61B 3/102
                                                          600/425
2013/0296695 A1   11/2013 Spencer et al.

\* cited by examiner

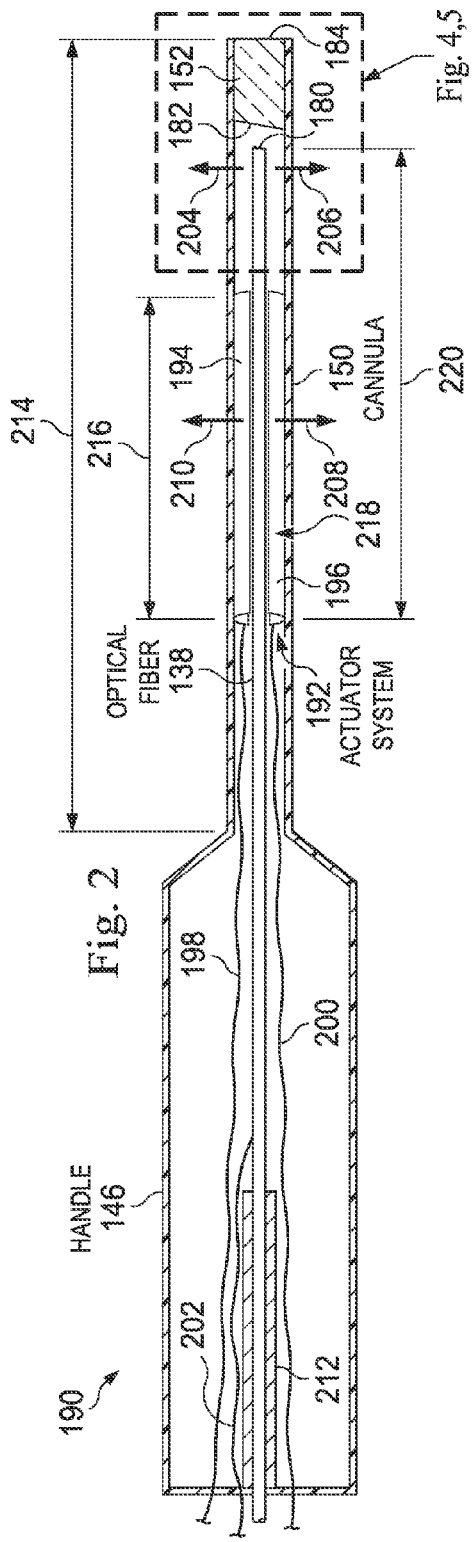
Fig. 2
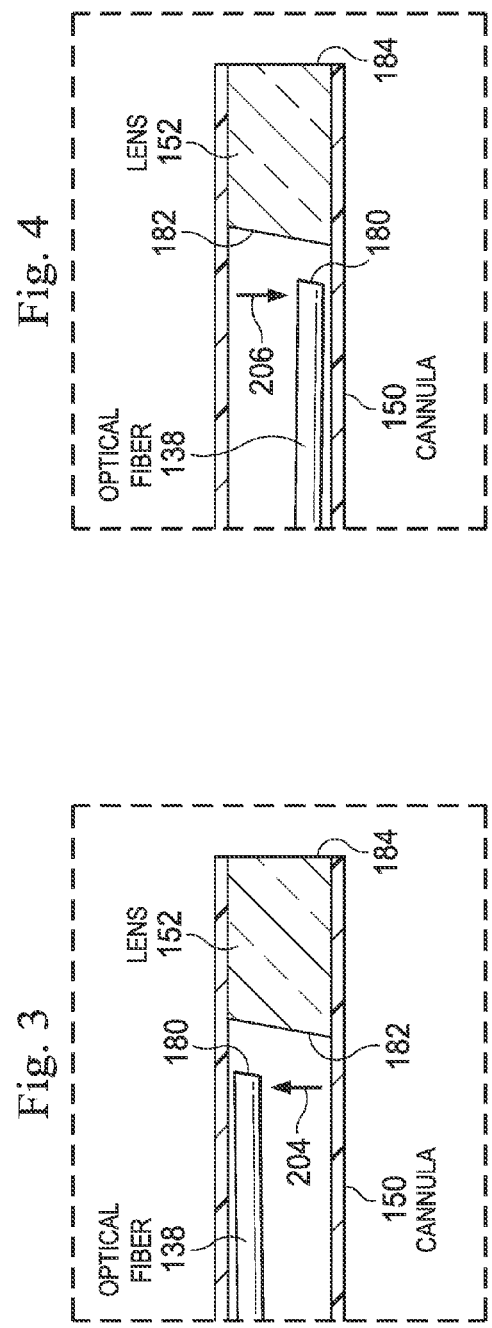
Fig. 3
Fig. 4

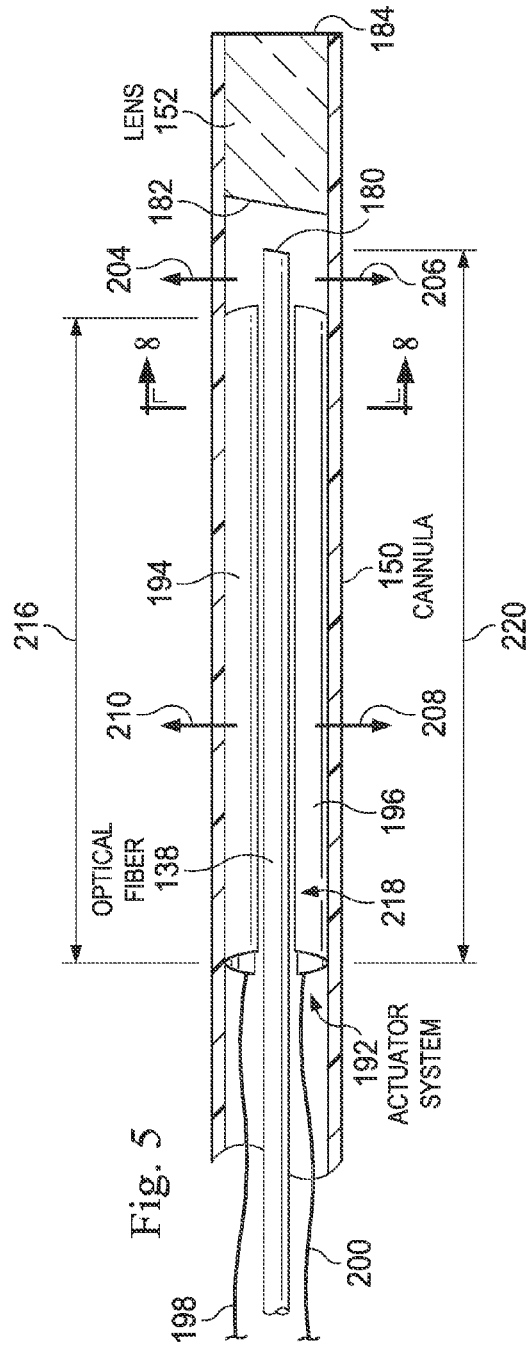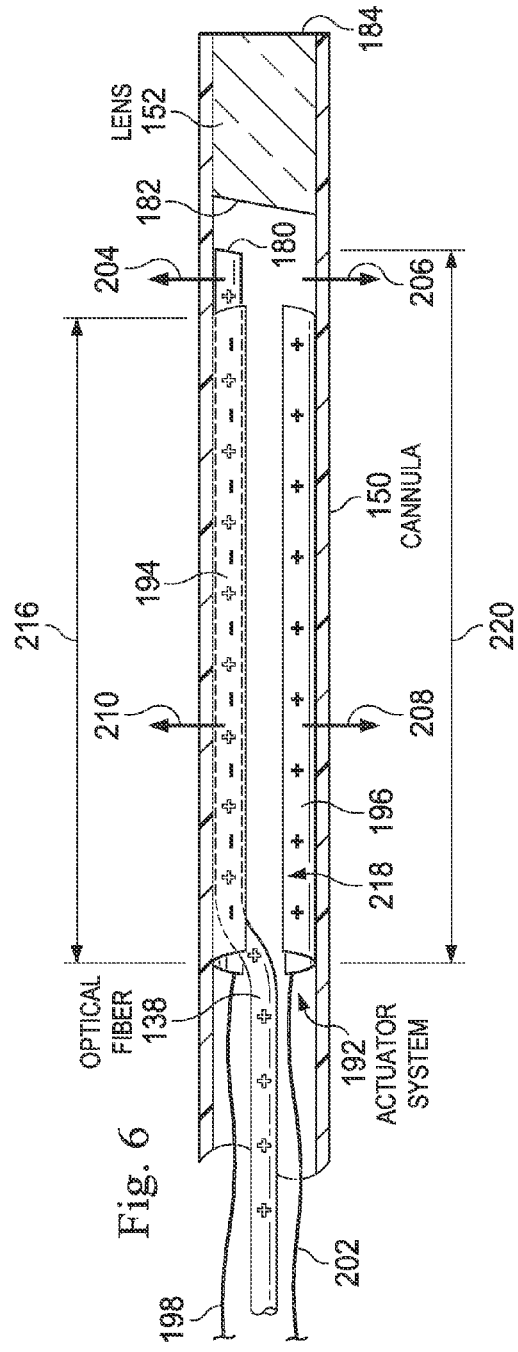

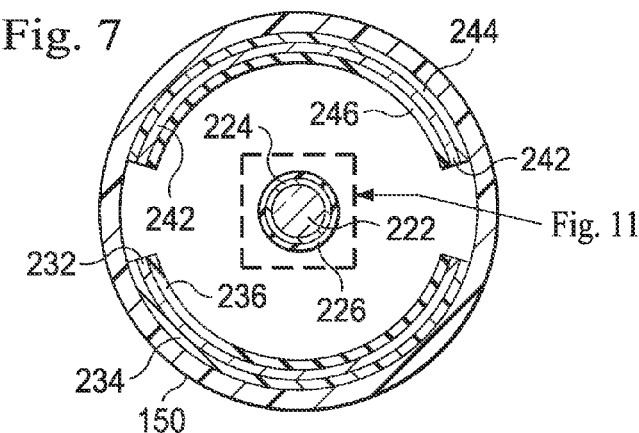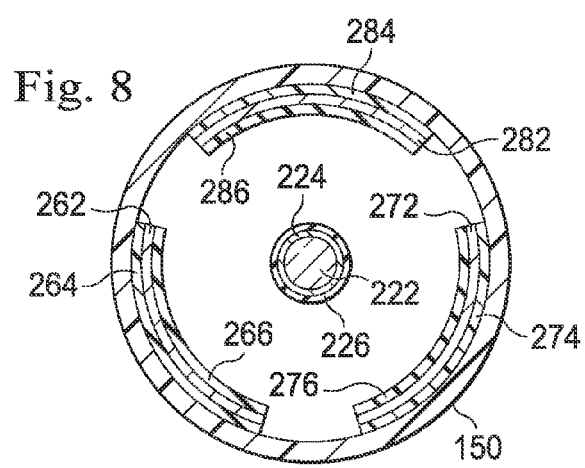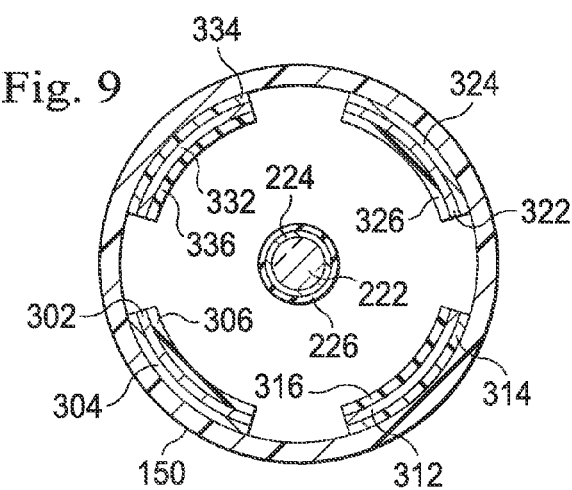

IMAGING PROBES AND ASSOCIATED DEVICES, SYSTEMS, AND METHODS UTILIZING ELECTROSTATIC ACTUATORS

TECHNICAL FIELD

Embodiments disclosed herein are related to devices, systems, and methods for scanning tissue with an optical coherence tomography (OCT) probe, and more particularly, to devices, systems, and methods that utilize an OCT probe having a displaceable fiber for ophthalmic imaging.

BACKGROUND

Optical Coherence Tomography (OCT) systems are used to capture and generate images of patient tissue layers. These systems often include OCT probes that can invasively penetrate tissue to obtain visualization of tissue within a patient. In ophthalmology, OCT probes are used to obtain detailed images of tissue about the eye or even forming a part of the eye, such as the retina.

In use, an optical light beam is directed through the probe at the tissue. A small portion of this light reflects from sub-surface features of the tissue and is collected through the same probe. Most of the light is not reflected but, rather, diffusely scatters at large angles. In conventional imaging, this diffusely scattered light contributes background noise that obscures an image. However, in OCT, a technique called interferometry records the optical path lengths of received photons, and provides data that rejects most of the photons that scatter multiple times before detection. This results in images that are clearer and that extend in the depth of the tissue.

The OCT probes often include a projecting cannula that can invasively penetrate patient tissue. The probe scans tissue by refracting the optical light beam through a lens disposed at an end of the cannula. A scan can include moving an optical fiber back and forth within the cannula to direct the light beam through the lens and at the tissue at different angles. The length and small diameter of the cannula make it difficult to move the fiber back and forth within the cannula. Further, the small amount of available space within the probe limits the types of actuators that can be utilized. Further still, the OCT probes and associated systems must be capable of being manufactured in a cost-effective manner, which includes the ability to make the probe as a disposable, one-time use device in some implementations.

SUMMARY

Embodiments disclosed herein are related to devices, systems, and methods that utilize at least one charged electrode to impart motion to an optical fiber positioned within an imaging probe by an electrostatic force.

Consistent with some embodiments, an ophthalmic imaging probe is provided. The probe can include a handle; a cannula coupled to the handle; an optical fiber positioned at least partially within the handle and the cannula, the optical fiber configured to receive an imaging light from an imaging light source and guide the imaging light to an optical element positioned within the distal portion of the cannula; and an actuator system configured to impart motion to the optical fiber, the actuator system including an electrode positioned within the cannula and configured to impart motion to the optical fiber by selectively imparting an electric charge to at least one of the electrode and the electrically conductive layer of the optical fiber.

The electrode can extend along at least one third (⅓) of a longitudinal extent of the cannula. The actuator system can further include a second electrode positioned within the cannula. The actuator system can further include a third electrode or a multiplicity of electrodes positioned within the cannula. The electrode and the second electrode can be symmetrically disposed around the optical fiber. The optical fiber can include an electrically conductive layer and/or an insulating layer. The electrically conductive layer can be disposed between the optical fiber and the insulating layer. The insulating layer can include a dielectric material. An interior-facing surface of the electrode can include an insulating layer. An exterior-facing surface of the electrode can include an insulating layer. The actuator system can be configured to impart motion to the optical fiber to scan the imaging light over a one-dimensional or a two-dimensional scanning pattern. An actuator system including at least one electrode can implement a one-dimensional scan pattern. An actuator system including two, three, four, or more electrodes can implement a two-dimensional scan pattern. The one-dimensional scan pattern can include at least one of a line and an arc. The two dimensional scanning pattern can include at least one of a spiral, a raster, a constant-radius asterisk pattern, a multiple-radius asterisk pattern, and a multiply folded path. The optical element can include a gradient index (GRIN) lens. The optical element can be mechanically coupled to a distal end of the optical fiber so that the optical element moves with the distal end of the optical fiber. The actuation system can be configured to impart motion to the optical fiber to scan the imaging light along a scanning pattern with a linear extent at a target biological tissue between 1 mm and 5 mm at a distance between 5 mm and 10 mm from a distal end of the handle.

Consistent with some embodiments, an ophthalmic imaging system is provided. The system can include an imaging light source configured to generate an imaging light; an optical guide in optical communication with the imaging light source, the optical guide configured to receive the generated imaging light from the imaging light source; and a probe in optical communication with the optical guide, the probe including a handle; a cannula coupled to the handle; an optical fiber positioned at least partially within the handle and the cannula, the optical fiber including an electrically conductive layer, wherein the optical fiber is configured to receive the imaging light from the optical guide and guide the imaging light to an optical element positioned within the distal portion of the cannula; and an actuator system configured to impart motion to the optical fiber, the actuator system including an electrode positioned within the cannula and configured to impart motion to the optical fiber by selectively imparting an electric charge to at least one of the electrode and the electrically conductive layer of the optical fiber.

The system further includes a controller in communication with the light source, the controller configured to control actuation of the imaging light source for an optical coherence tomography (OCT) imaging procedure. The controller can be further configured to process data obtained by the probe and output imaging data to a display in communication with the controller. The controller can be further configured to selectively cause a voltage to be applied to at least one of the electrically conductive layer of the optical fiber and the electrode such that at least one of the electrically conductive layer of the optical fiber and the electrode acquires an electrical charge. The optical fiber can include an insulating layer such that the electrically conductive layer is disposed between the insulating layer and the optical fiber. The insulating layer can include a dielectric material.

Consistent with some embodiments, a method of ophthalmic imaging is provided. The method can include applying a first voltage to an electrode positioned within a housing of an ophthalmic probe such that the electrode acquires an electrical charge having a first polarity; and applying a second voltage to an electrically conductive layer of an optical fiber positioned within the housing of the ophthalmic probe such that the electrically conductive layer acquires an electrical charge having a second polarity, the optical fiber further including an insulating layer configured to prevent electrical communication between the electrode and the electrically conductive layer of the optical fiber; wherein an electrostatic force resulting from the electrode acquiring the electrical charge having the first polarity and the electrically conductive layer of the optical fiber acquiring the electrical charge having the second polarity causes the optical fiber to scan an imaging light passing through the optical fiber across an optical element positioned within a distal portion of the housing.

Additional aspects, features, and advantages of the present disclosure will become apparent from the following detailed description.

BRIEF DESCRIPTION OF THE DRAWINGS

FIG. 2 is a stylized illustration of a cross-sectional side view of an imaging probe in accordance with an aspect of the present disclosure.

FIG. 3 is a stylized illustration of a cross-sectional view of a distal portion of the imaging probe of FIG. 2 showing an optical fiber of the imaging probe in a first position in accordance with an aspect of the present disclosure.

FIG. 4 is a stylized illustration of a cross-sectional view of the distal portion of the imaging probe of FIG. 2, similar to that of FIG. 3, but showing the optical fiber in a second position in accordance with an aspect of the present disclosure.

FIG. 5 is a stylized illustration of a cross-sectional side view of the cannula of the imaging probe of FIG. 2 in accordance with an aspect of the present disclosure.

FIG. 6 is a stylized illustration of a cross-sectional side view of the cannula of the imaging probe of FIG. 2 in accordance with another aspect of the present disclosure.

FIG. 7 is a stylized illustration of a cross-sectional back view of an imaging probe along section line 8-8 of FIG. 5 in accordance with an aspect of the present disclosure.

FIG. 8 is a stylized illustration of a cross-sectional back view of an imaging probe, similar to that of FIG. 7, but showing multiple electrodes in accordance with an aspect of the present disclosure.

FIG. 9 is a stylized illustration of a cross-sectional back view of an imaging probe, similar to that of FIG. 7, but showing multiple electrodes in accordance with another aspect of the present disclosure.

Figure 1:
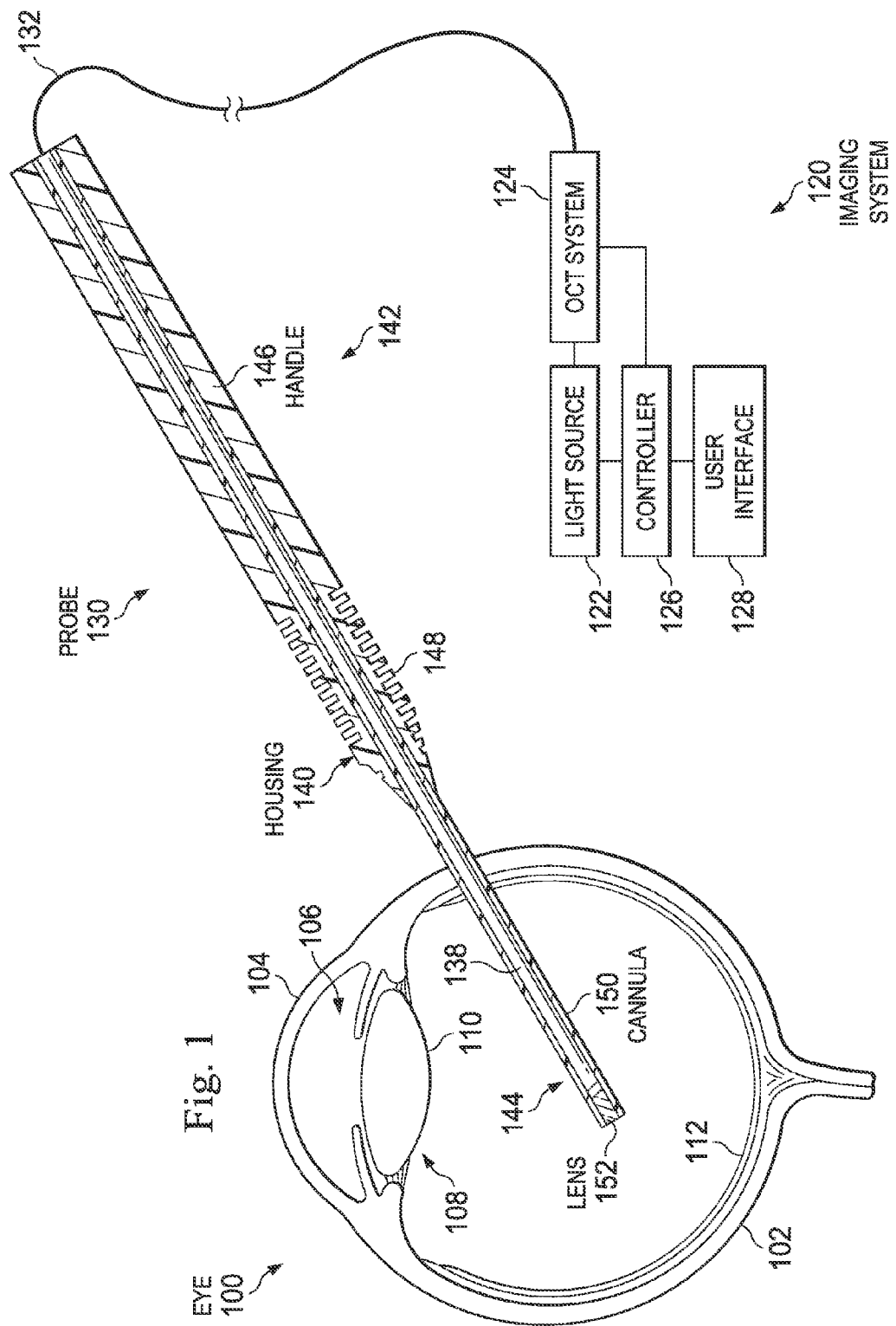
FIG. 1 is a diagrammatic schematic view of an eye under treatment and an exemplary OCT imaging system in accordance with an aspect of the present disclosure.

In the drawings, elements having the same designation have the same or similar functions.

DETAILED DESCRIPTION

In the following description specific details are set forth describing certain embodiments. It will be apparent, however, to one skilled in the art that the disclosed embodiments can be practiced without some or all of these specific details. The specific embodiments presented are meant to be illustrative, but not limiting. One skilled in the art can realize other material that, although not specifically described herein, is within the scope and spirit of this disclosure. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment can be combined with the features, components, and/or steps described with respect to other embodiments of the present disclosure. For the sake of brevity, however, the numerous iterations of these combinations will not be described separately.

The present disclosure relates generally to OCT probes, OCT systems, and methods that scan tissue to obtain an OCT image. The probe can include a cannula configured to invasively penetrate patient tissue, such as the globe of an eye. The cannula can house a lens and an optical fiber. The fiber directs light through the lens and captures reflected light that passes back through the lens. To obtain a scan of an area or a line of tissue, rather than merely a point, the fiber can be moved within the cannula relative to the lens to cause the light emerging from the lens to scan across the desired pattern. Because the cannula that penetrates the patient tissue is desirably small in cross-section, moving the fiber within the cannula is difficult. The small amount of available space within the probe limits the types of actuators that can be utilized to impart movement to the fiber. In some instances it is desirable to manufacture the probe, or at least a portion thereof, as a disposable component, which requires product designs having cost-effective manufacturing techniques.

Exemplary aspects described herein utilize a technique of moving all or some portion of the fiber within the probe using an actuator system positioned within the probe that overcomes one or more of the problems or limitations of previous approaches. In some aspects described herein, the actuator system can include a charged electrode. The actuation of the optical fiber can be achieved by creating an electrostatic or Coulomb force between the optical fiber and the charged electrode. The optical fiber can be attracted (e.g., drawn towards) or repulsed (e.g., pushed away) from the electrode depending on the respective charges of one or both of the optical fiber and the electrode. In some aspects, the actuator system can be configured to impart amplified motion to a distal section of the optical fiber. For example, the optical fiber can be positioned within the probe so that a distal end of the optical fiber extends past a distal end of an electrode such that motion imparted to the distal section of the optical fiber is amplified relative to movement of a portion of the optical fiber proximate to and/or longitudinally coextensive with the electrode.

In some aspects, at least a portion of the optical fiber (e.g., a distal portion) includes an electrically conductive coating. A voltage can be applied to the electrically conductive coating of the optical fiber such that electrically conductive conduct is either positively or negatively charged. The optical fiber can include an insulating layer. The insulating layer can include a dielectric material.

In some aspects, the charged electrode can be positioned in an interior of the cannula of the optical probe. In some aspects, multiple distinct electrodes can be provided. The multiple electrodes can be positioned annularly around the optical fiber in an interior of the cannula. For example, the actuator system can have first and second electrodes extending longitudinally along the cannula and spaced 180° apart from one another. In some aspects, the first electrode and the electrically conductive coating of the optical fiber can be charged with opposite polarities to create an attractive electrostatic force. The optical fiber can be drawn towards the first electrode by the attractive electrostatic force. In some aspects, additionally, the second electrode can be charged with the same polarity as the electrically conductive coating of the optical fiber to create a repulsive electrostatic force. The optical fiber can be pushed away from the second electrode (and towards the first electrode) by the repulsive electrostatic force. The optical fiber and the two electrodes can be electrically connected to a controller providing voltage and electrical charge to the three circuits (e.g., the optical fiber and the two electrodes).

In some aspects, the electrodes can be electrically isolated from the cannula and/or the optical fiber by an insulating and/or dielectric layer or coating between electrodes and the cannula and/or the optical fiber. In some aspects, the electrodes can be electrically isolated by an insulating layer. The insulating layer can include a dielectric material.

In some aspects, to oscillate the optical fiber, the controller can provide a positive voltage to the fiber and charge it with a positive charge during one-half of a frequency cycle. One electrode in the cannula can be applied a negative voltage that charges it with a negative charge. The other electrode can have a positive voltage applied that charges it with a positive charge. The oppositely charged optical fiber and one of the electrodes are attracted to each other because of the opposite polarity electric fields. The optical fiber and the electrode that is charged the same are repelled by each other because of the same polarity electrical fields. The second half of the cycle can be a repeat of the first half with the polarity of the optical fiber switched or the polarities of the electrodes switched. In some embodiments, the polarity of the fiber can remain the same throughout an entire cycle while the polarity of the electrodes is alternated during each half cycle.

In some aspects, physically compact and inexpensive actuator systems for the OCT probe are provided. In some aspects, the actuator systems provide the ability to move a distal tip of the optical fiber in two dimensions during a scanning process.

FIG. 1 is a diagrammatic schematic view of an arrangement illustrating aspects of the present disclosure. In particular, an eye 100 under treatment is shown. The eye 100 includes sclera 102, a cornea 104, an anterior chamber 106, and a posterior chamber 108. A capsular bag 110 is illustrated in the posterior chamber 108. The eye 100 further includes a retina 112.

An exemplary imaging system 120 is also illustrated in FIG. 1. As discussed in greater detail below, imaging system 120 is configured to image portions of the eye 100, such as the retina 112. The imaging system 120 can include a light source 122, an optical coherence tomography (OCT) system 124, a controller 126, a user interface 128, and a probe 130. The light source 122 is configured to provide imaging light that will be directed onto the target biological tissue by the probe 130. The light source 122 can be made up of superluminescent diodes, ultra-short pulsed lasers, or supercontinuum lasers that provide relatively long wavelength light, such as between 700 nm and 1400 nm, between 700 nm and 900 nm, between 900 nm and 1200 nm, between 1000 nm and 1100 nm, between 1250 nm and 1450 nm, or between 1400 nm and 1600 nm. Imaging light reflected from the target biological tissue and captured by the probe 130 is utilized to generate images of the target biological tissue.

The OCT system 124 is configured to split the imaging light received from the light source 122 into the imaging beam that is directed onto the target biological tissue by the probe 130 and a reference beam that can be directed onto a reference mirror. The OCT system 124 can be a spectral domain or a time domain system. The OCT system 124 is further configured to receive the imaging light reflected from the target biological tissue and captured by the probe 130. The interference pattern between the reflected imaging light and the reference beam is utilized to generate images of the target biological tissue. Accordingly, the OCT system 124 can include a detector configured to detect the interference pattern. The detector can include Charge-Coupled Detectors (CCDs), pixels, or an array of any other type of sensor(s) that generate an electric signal based on detected light. Further, the detector can include a two-dimensional sensor array and a detector camera.

The controller 126 can include a processor and memory, which may include one or more executable programs for controlling aspects of the light source 122, the user interface 128, and/or the probe 130, and for executing and performing functions and processes to carry out an OCT imaging procedure. For example, the controller 126 is configured to control an actuation system of probe 130 configured to scan the imaging beam across the target biological tissue in some implementations.

One or more of the light source 122, the OCT system 124, the controller 126, and the user interface 128 can be implemented in separate housings communicatively coupled to one another or within a common console or housing. For example, in some implementations the light source 122, the OCT system 124, and the controller are positioned within a console that is communicatively coupled to the user interface 128. The user interface 128 can be carried on or form part of the console. Further, the user interface 128, or at least part(s) thereof, can be separate from the console. The user interface 128 can include a display configured to present images to a user or a patient, and display tissue scanned by the probe 130 during an OCT imaging procedure. The user interface 128 can also include input devices or systems, including by way of non-limiting example, a keyboard, a mouse, a joystick, a touchscreen, dials, and buttons, among other input devices.

The probe 130 is in optical communication with OCT system 124. In that regard, the probe 130 is configured to present light from the light source 122 that passes through OCT system 124 onto the target biological tissue for the purpose of imaging the tissue. Further, the probe can be in electrical communication with the controller 126. In that regard, the controller 126 can control an actuation system of the probe 130 via electrical signals sent to the probe 130 in order to cause the actuation system to scan the imaging beam across the target biological tissue. A cable 132 can connect the probe 130 to the OCT system 124 and/or the controller 126. In that regard, cable 132 can include optical fiber(s), electrical conductor(s), insulator(s), shield(s), and/or other features configured to facilitate optical and/or electrical communication between the probe 130 and the OCT system 124 and/or the controller 126. Further, it is understood that cable 132 can include multiple, separate cables. For example, in some instances an optical cable connects the probe 130 to OCT system 124 and a separate electrical cable connects the probe 130 to controller 126.

Controller 126 can be in electrical communication with one or more electrodes (e.g., electrodes 194 and 196 of FIG. 3, electrodes 232 and 242 of FIG. 8, electrodes 262, 272, and 282 of FIG. 9, electrodes 302, 312, 322, and 332 of FIG. 10, etc.) and/or an electrically conductive layer of the optical fiber 138. Controller 126 can apply a voltage to and/or cause a positive or negative voltage to be applied to (e.g., from a voltage source of imaging system 120, such as a battery, etc.) the one or more electrodes and/or the electrically conductive layer of the optical fiber 138. In that regard, imaging system 120 can include one or more voltage sources (e.g., one voltage source for each of the electrodes and/or the electrically conductive layer of the optical fiber 138).

The imaging system 120 can include a connector that is configured to facilitate removable coupling of the probe 130 and/or the cable 132 with the OCT system 124 and/or the controller 126. The connector is configured to facilitate mechanical, optical, and/or electrical coupling of the probe 130 and/or the cable 132 with the OCT system 124 and/or the controller 126. For example, an optical fiber 138 extending along the length of the probe 130 is optically coupled to the OCT system 124 via the coupling of the connector with the OCT system 124. The optical fiber 138 can be a single fiber or a fiber bundle. In some embodiments, the connector is configured to threadingly engage with the OCT system 124 and/or the controller 126. However, it is understood that any type of selective engagement feature(s) or connectors can be utilized, including without limitation press fit, luer lock, threads, and combinations thereof, among other connection types. In some aspects, connector is located proximate to the OCT system 124 and/or the controller 126. The selective engagement of the connector at the OCT system 124 and/or the controller 126 allows the entire probe 130 to be a disposable component configured for use in a single procedure.

The probe 130 is sized and shaped to be handled by a surgeon and to protrude into a body of the patient. The probe 130 includes a housing 140 having a proximal portion 142 and a distal portion 144. The proximal portion 142 of the housing 140 can be sized and shaped for handheld grasping by a user. For example, the proximal portion 142 of the housing 140 can define a handle 146. The handle 146 can be sized and shaped for grasping by a single hand of the user. Further, the handle 146 can include a textured surface 148 (e.g., roughened, knurled, projections/recesses, tapers, other surface features, and/or combinations thereof) to enhance the user's grip on the handle 146. In use, the user controls the position of the distal portion 144 of the housing 140 by maneuvering the handle 146 such that the imaging light beam is directed towards the target biological tissue.

The distal portion 144 of the probe 130 can be sized and shaped for insertion into the eye 100 to be treated. In the illustrated embodiment of FIG. 1, the distal portion 144 of the probe 130 includes a cannula 150. The cannula 150 can be sized and shaped for insertion through the sclera 102 of the eye 100 to facilitate imaging of the retina 112. The cannula 150 can be integrally formed with the handle 146 as part of the housing 140. Alternatively, the cannula 150 and the handle 146 can be separate components fixedly secured to one another to form the housing 140. An optical element 152, such as a lens, can be secured within the distal end of the cannula 150. The optical element 152 is configured to focus the imaging light onto the target biological tissue, such as the retina 112. The optical element 152 can be, e.g., a gradient index (GRIN) lens, any other suitable lens, any suitable optical component(s), or a combination thereof. Depending upon the embodiment, the gradient index can be spherical, axial, or radial. The optical element 152 can also be a spherical lens. Other lens shapes can be used.

As will be discussed in greater detail below, the optical fiber 138 is moved with respect to the optical element 152 by an actuator system disposed within the probe 130 to cause the imaging beam—as focused by the optical element 152—to scan across a portion of the target biological tissue. FIGS. 2 and 5-10 described below illustrate various exemplary embodiments of actuator systems in accordance with the present disclosure. In that regard, it is understood that the actuator systems of the present disclosure can be positioned within the handle 146, within the cannula 150, and/or combinations thereof to move the optical fiber 138 across a desired scan pattern.

The distance of the focal point of the imaging beam from the distal end of the probe 130 can be determined by the optical element 152, a gap distance between the distal tip of the optical fiber 138 and a proximal face of the optical element 152, a numerical aperture of the optical fiber 138, and/or the wavelength of light of the imaging beam. For example, in some instances the focal power of the optical element 152 and/or the gap distance is selected to have a focus depth corresponding to likely distance of the distal end of the probe 130 from the target biological tissue during use. In some implementations of the probe 130 for retinal imaging, the focal point of the imaging beam can be between 1 mm and 20 mm, between 5 mm and 10 mm, between 7 mm and 8 mm, or approximately 7.5 mm beyond the distal end of the probe 130.

The discussion below generally refers to FIGS. 2 and 5. FIG. 2 is a stylized illustration of a cross-sectional side view of an imaging probe 190 in accordance with an aspect of the present disclosure. FIG. 5 is a stylized illustration of a cross-sectional side view of the cannula of the imaging probe of FIG. 2 in accordance with an aspect of the present disclosure.

As shown, the optical fiber 138 extends along the length of the probe 190 through the handle 146 and the cannula 150. The optical fiber 138 can be cantilevered. That is, a proximal portion of the optical fiber 138 can be fixed on a proximal portion of the probe 190, and a distal portion 218 of the optical fiber 138 is movable with respect to the handle 146 and/or the cannula 150. In the illustrated embodiment, at least a portion of an actuator system 192 is positioned within the cannula 150. The actuator system 192 is configured to impart motion to the optical fiber 138 such that a distal end 180 of the optical fiber 138 moves with respect to the cannula 150 and optical element 152 that is fixedly secured to the cannula. More specifically, the distal end 180 of the optical fiber 138 can be moved with respect to the optical element 152 to scan the imaging beam across a desired pattern with respect to the target biological tissue.

The optical element 152 is configured to focus the imaging beam received from the optical fiber 138 onto the target biological tissue. In that regard, the optical element 152 includes a proximal face 182 and a distal face 184. The imaging beam enters the optical element 152 through proximal face 182 and leaves the optical element 152 through distal face 184. As shown, the proximal face 182 of the optical element 152 can extend at an oblique angle with respect to the longitudinal axis of the cannula 150. By having the proximal face 182 oriented at an oblique angle, the amount of reflection resulting from the imaging beam entering the optical element 152 can be reduced. In other embodiments, the proximal face 182 extends perpendicular to the longitudinal axis of the cannula 150.

The distal end 180 the optical fiber 138 can be spaced from the proximal face 182 of the optical element 152. In that regard, the spacing between the distal end 180 of the optical fiber 138 and the proximal face 182 of the optical element 152 can be selected to achieve a desired optical performance (e.g., focal distance, focus size, etc.). The spacing between the distal end 180 of the optical fiber 138 and the proximal face 182 of the optical element 152 can also be selected to allow a desired range of motion of the optical fiber 138 within the cannula 150 without physically contacting the optical element 152. The optical element 152 can be mechanically coupled to the distal end 180 of the optical fiber 138 so that the optical element 152 moves with the distal end 180 of the optical fiber 138.

The actuator system 192 is configured to impart motion to the optical fiber 138 such that the distal end 180 of the optical fiber 138 can be moved with respect to the optical element 152 to scan the imaging beam across a desired pattern with respect to the target biological tissue. The actuator system 192 can include at least one electrode (e.g., one, two, three, four, or more electrodes). More specifically, the actuator system 192 is configured to generate an electrostatic force between the optical fiber 138 and the electrode by applying a voltage to and charging the electrode. By selectively charging the electrode, the optical fiber 138 can be oscillated with respect to optical element 152 during a scanning process.

In some embodiments, all or some portion of the optical fiber 138 within the probe 190 (e.g., the distal end 180) moves, for example, between 10 µm and 500 µm, between 50 µm and 500 µm, between 100 µm and 400 µm, or between 100 µm and 300 µm across the proximal face 182 of the optical element 152. The resulting optical scan is projected to the target biological tissue at a distance between, for example, 1 mm and 20 mm from the distal end of the cannula 150 (e.g., the focal point of the imaging beam, as described above). The linear extent of the imaging beam at the target biological tissue can be between 1 mm and 10 mm, between 1 mm and 8 mm, or between 1 mm and 5 mm. For example, there can be between approximately 50× and approximately 1000× multiplication of the distance the fiber moves across the proximal face 182 of the optical element 152 compared to the linear extent of the imaging beam at the target biological tissue.

The one or more electrodes of actuator system 192 can be made of or can include an electrically conductive material such as one or more metals. The electrode can be made of a material that is not electrically conductive but that is covered by an electrically conductive layer. The electrically conductive layer can be coupled to the material that is not electrically conductive using chemical processes such as electroplating, electroless plating, spraying, hot dipping, chemical vapor deposition, ion vapor deposition, etc.; a suitable adhesive (e.g., glue, epoxy, etc.); mechanical connection; and/or combinations thereof. The shape of the electrode can be planar, curved, or some combination thereof.

An exterior of at least a portion of the optical fiber 138 can include an electrically conductive layer (e.g., the entirety of optical fiber 138 in an interior of probe 190 or the distal portion 218 of the optical fiber 138). It is understood, that when an optical fiber is described as including an electrically conductive layer, the electrically conductive layer can be a component that is distinct from the optical fiber itself, such as a coating, sleeve, etc., that is applied and/or otherwise coupled to the optical fiber. The electrically conductive layer can be coupled to the optical fiber 138 using chemical processes such as electroplating, electroless plating, spraying, hot dipping, chemical vapor deposition, ion vapor deposition, etc.; a suitable adhesive (e.g., glue, epoxy, etc.); mechanical connection; and/or combinations thereof. The electrically conductive coating can include gold, aluminum, etc.

One or more electrodes of actuator system 192 and/or optical fiber 138 are in electrical communication with a controller (e.g., controller 126 of FIG. 1) via one or more conductors. The controller can be configured to apply a voltage to and/or cause a voltage to be applied to the electrode and/or the electrically conductive coating of optical fiber 138. The voltage can have a polarity (e.g., a positive voltage or a negative voltage). When the voltage is applied, the electrode and/or the electrically conductive coating of the optical fiber 138 can acquire a charge with a polarity (e.g., a positive charge or a negative charge). For example, when a positive voltage is applied to an electrode, the electrode acquires a positive charge. For example, when a negative voltage is applied to an electrode, the electrode acquires a negative charge. The magnitude of the voltage applied to the electrode and/or the optical fiber 138 can be the same or different (e.g., the voltage applied to one can be greater than or less than the voltage applied to the other). When a voltage is applied to the electrode and/or optical fiber 138, each is statically charged and has an electric field associated therewith. The electrode and/or optical fiber 138 are not part of a complete circuit. In that regard, the electrode and/or optical fiber 138 can be considered capacitor-like in that each maintains a charge until it is discharged (e.g., by contact with a metal or metallized object that completes the circuit, through circuitry in the controller, etc.).

An electrostatic or Coulomb force can arise between charged components. Attractive electrostatic forces arise between oppositely-charged components (e.g., a negatively-charged electrode and a positively-charged optical fiber). Repulsive electrostatic forces arise between like-charged components (e.g., a positively-charged electrode and a positively-charged optical fiber). Because stroke distance or the distance that the distal end 180 of the optical fiber 138 travels during a frequency cycle (e.g., the inside cannula diameter minus the fiber diameter) is relatively small, Coulomb's Law provides that the electric fields associated with the one or more electrodes of actuator system 192 and/or optical fiber 138 are relatively strong, as are the electrostatic forces.

Movement of the distal end 180 of the optical fiber 138 can be caused by selectively charging the electrode and/or optical fiber 138 with different polarities such that the attractive and/or repulsive electrostatic forces are generated between one or more of these elements of probe 190. That is, a voltage can be applied to and/or a charge is acquired by one or more of the electrode and/or optical fiber 138. Based on the resulting electrostatic forces, optical fiber 138 can be pushed (by repulsive electrostatic forces), pulled (by attractive electrostatic force), or both, in directions 210 or 208. This causes movement of distal end 180 of optical fiber 138 in directions indicated by arrows 204 or 206.

In some embodiments, the actuator system 192 includes one electrode. For example, the electrode can be positioned above the optical fiber. The optical fiber can be oscillated during a scanning process by selectively charging and discharging the electrode and/or the optical fiber. During the first half of the frequency cycle, the electrode and the optical fiber can be charged such that attractive electrostatic forces are generated and the optical fiber moves towards the electrode. During the second half of the frequency cycle, the electrode and/or optical fiber can be discharged such that the optical fiber moves in the direction opposite the electrode because of, e.g., the weight of the optical fiber, elastic restoring forces developed in the optical fiber during the first half of the frequency cycle, and/or one or more restoring elements. The direction of movement during the second half of the frequency cycle can be opposite the direction of movement during the first half. In this manner, optical fiber 138 can be oscillated relative to optical element 152 during the scanning process.

In some embodiments, the actuator system 192 includes one electrode. During the first half of the frequency cycle, the optical fiber 138 and the electrode can be charged such that an attractive or repulsive electrostatic force is generated. The electrostatic force can cause movement of optical fiber 138, and in particular, movement of distal end 180 relative to optical element 152. During the second half of the frequency cycle, the optical fiber 138 and the electrode can be charged such that the opposite electrostatic force (compared to the first half of the frequency cycle) is generated. The electrostatic force can cause movement of optical fiber 138, and in particular, movement of distal end 180 relative to optical element 152. The direction of movement during the second half of the frequency cycle can be opposite the direction of movement during the first half. In this manner, optical fiber 138 can be oscillated relative to optical element 152 during the scanning process.

In some embodiments, the optical fiber 138 is not charged during a scanning process. Rather, at least one electrode of the actuator system 192 is charged. Thus, in some embodiments, the optical fiber 138 does not include an electrically conductive layer. The optical fiber 138 can be oscillated during a scanning process without being charged. For example, the optical fiber 138 can be a glass fiber. Glass is likely to obtain a positive charge, as indicated in the triboelectric series. For example, during a first half of a frequency cycle, a negative voltage can be selectively applied to the electrode such that the electrode acquires a negative charge. Because of charge-induced charge separation in the optical fiber 138, optical fiber 138 acquires a positive charge, which generates attractive electrostatic forces between optical fiber 138 and the electrode. For example, during a second half of the frequency cycle, a positive voltage can be selectively applied to the electrode to generate repulsive electrostatic forces between optical fiber 138 and the at least one electrode. The direction of movement during the second half of the frequency cycle can be opposite the direction of movement during the first half. In this manner, optical fiber 138 can be oscillated relative to optical element 152 during a scanning process.

In some embodiments, the actuator system 192 includes two electrodes, though only one electrode is charged at a given time during the scanning process. The optical fiber 138 and one of the electrodes are charged during the first and/or second halves of the frequency cycle. During the first half of the frequency cycle, the optical fiber 138 and the one electrode can be charged such that an attractive or repulsive electrostatic force is generated. The electrostatic force can cause movement of optical fiber 138, and in particular, movement of distal end 180 relative to optical element 152. During the second half of the frequency cycle, the optical fiber 138 and the other of the electrodes can be charged such that an attractive or repulsive electrostatic force is generated. The electrostatic force can cause movement of optical fiber 138, and in particular, movement of distal end 180 relative to optical element 152. The direction of movement during the second half of the frequency cycle can be opposite the direction of movement during the first half. In this manner, optical fiber 138 can be oscillated relative to optical element 152 during a scanning process.

In some embodiments, the actuator system 192 includes two electrodes, and both electrodes are charged at a given time during the scanning process. The optical fiber 138 and both electrodes are charged during the first and/or second halves of the frequency cycle. During the first half of the frequency cycle, the optical fiber 138 and one electrode can acquire a first polarity charge while the other electrode acquires a second polarity charge. Thus, attractive electrostatic forces are generated between the optical fiber 138 and the oppositely charged electrode; repulsive electrostatic forces are generated between the optical fiber 138 and the similarly charged electrode. The electrostatic forces cause movement of the optical fiber 138. During the second half of the frequency cycle, the polarity of the electrodes can be switched while the polarity of the optical fiber 138 is kept the same and/or the polarity of the optical fiber 138 can be switched while the polarity of the electrodes is kept the same. Thus, electrostatic forces that are in opposite directions compared to the first half of the frequency cycle are generated. The electrostatic forces cause movement of the optical fiber 138. The direction of movement during the second half of the frequency cycle can be opposite the direction of movement during the first half. In this manner, optical fiber 138 can be oscillated relative to optical element 152 during a scanning process.

In the illustrated embodiments of FIGS. 2 and 5, two electrodes 194 and 196 are provided. That is, actuator system 192 can include a first electrode and a second electrode. The shape of electrodes 194 and 196 can follow the shape of cannula 150. That is, electrode 194 and/or 196 can extend in a curved manner around at least a portion of an interior perimeter of cannula 150. The electrodes 194 and 196 can be symmetrically disposed around the optical fiber 138. For example, electrodes 194 and 196 can be disposed 180° apart. The angle separating adjacent electrodes of actuator system 192 can be between 0° and 360°, 30° and 330°, 45° and 315°, 60° and 300°, 90° and 270°, 120° and 240°, 135° and 225°, 150° and 210°, and 175° and 195°. In some embodiments, adjacent electrodes are separated by 90°, 120°, or 180°.

The electrodes 194 and 196 can extend longitudinally along cannula 150. Cannula 150 can have a longitudinal extent or length 214. Electrodes 194 and/or 196 can have a longitudinal extent or length 216. The electrodes 194 and 196 can extend along at least one fourth (¼), one third (⅓), one half (½), three fourths (¾), or more of a length of the cannula. That is, the ratio of the length 216 of electrodes 194 and/or 196 to the length 214 of cannula 150 can be at least one fourth (¼), one third (⅓), one half (½), three fourths (¾), or more. In other embodiments, the ratio of length 216 to length 214 is greater than or less than these amounts. When electrodes 194 and 196 extend along cannula 150 for a longer distance, there is more area between the electrodes 194 and 196 and optical fiber 138 for producing greater and more evenly-distributed electrostatic forces. In some embodiments, electrodes 194 and 196 can extend the same distance longitudinally. In other embodiments, one of electrodes 194 and 196 can be longer than the other. In various embodiments, electrodes 194 and 196 can be wholly or partially provided in handle 146, cannula 150, and/or a combination thereof. Electrodes 194 and 196 can be fixedly secured to the probe 190 (e.g., handle 146, cannula 150, etc.)

using a suitable adhesive (e.g., glue, epoxy, etc.); mechanical connection; and/or combinations thereof.

The optical fiber 138 can be secured within the handle 146 such that the distal end 180 of the optical fiber 138 extends distally beyond the distal ends of the electrodes 194 and 196. In this manner, the distal end 180 of the optical fiber 138 is cantilevered from the electrodes 194 and 196. As a result, the motion profile of the distal end 180 of the optical fiber 138 is amplified relative to the motion profile of the portion of the optical fiber 138 that is proximate to and/or longitudinally coextensive with the electrodes 194 and 196. In other words, the movement of the distal end 180 of the optical fiber 138 is greater than the corresponding movement of the proximate/coextensive portion of the optical fiber 138 that moves when the optical fiber 138 and/or the electrodes 194 and 196 are charged. For example, when the proximate/coextensive portion of the optical fiber 138 is moved towards the electrode 194 (when attracted to the electrode 194 and/or repelled by the electrode 196) as indicated by arrow 210, the distal end 180 of the optical fiber 138 will move as indicated by arrow 204 a greater distance in the same direction. Similarly, the proximate/coextensive portion the optical fiber 138 is moved towards the electrode 196 (when attracted to the electrode 196 and/or repelled by the electrode 194) as indicated by arrow 208, the distal end 180 of the optical fiber will move as indicated by arrow 206 a greater distance in the same direction. The ratio of the movement of the distal end 180 of the optical fiber 138 to the movement of the proximate/coextensive portion of the optical fiber 138 can be between 1.01:1.0 and 10.0:1.0, between 1.1:1.0 and 5.0:1.0, or between 1.5:1.0 and 2.0:1.0.

Electrode 194, electrode 196, and/or optical fiber 138 can be in electrical communication with a controller (e.g., controller 126 of FIG. 1) via conductors 198, 200, and 202 respectively. During a frequency cycle of the actuator system 192, selectively causing the one or more electrodes and/or the optical fiber 138 to acquire an electric charge can generate electrostatic forces between the one or more electrodes and the optical fiber 138.

The actuator system 192 is configured to move optical fiber 138 (e.g., the distal portion 218, the distal end 180, etc.) from a neutral position to one or more activated positions. The distal portion 218 of the optical fiber 138 can define a segment of optical fiber 138 extending longitudinally from a point of probe 190 where electrodes 194 and/or 196 begin to the distal end 180 of the optical fiber 138. In various embodiments, length 216 of electrodes 194 and/or 196 is greater than, less than, or equal to the length of distal portion 218 of optical fiber 138. In some embodiments, length 220 of distal portion 218 is greater than length 216 of the electrodes such that the distal end 180 is positioned more distally in cannula 150 than a distal end of the electrodes 194 and/or 196.

The distal portion 218 that is being actuated can be described as a free length of optical fiber 138. The free length (e.g., length 220 of distal portion 218) can be variously chosen based on whether there is enough length to be actuated, the strength of the electrostatic forces, the diameter of the optical element 152, etc. For example, the distal portion 218 is selected to be long enough such that the electrostatic forces can overcome the molecular forces of optical fiber 138 that maintain the structural integrity and the linear/planar disposition of optical fiber 138. That is, the electrostatic forces can act over a sufficient length of optical fiber 138 and/or cause a sufficient bending moment to bend optical fiber 138 in directions 208 and/or 210. In some embodiments, the length 220 of distal portion 218, which is being actuated, can include between 1 mm and 15 mm, between 3 mm and 12 mm, and between 5 mm and 10 mm, etc., from the distal end 180 of the optical fiber 138.

In a neutral position, the optical fiber 138 can be positioned at any location within the lumen of the cannula 140. For example, all or some portion of the optical fiber 138 within the probe 190 can be coaxial with the longitudinal axis of the cannula 150 (as shown in, e.g., FIG. 2), proximate to and/or in contact with one wall of the cannula 150 (as shown in, e.g., FIGS. 3 and 4), proximate to and/or in contact with an electrode, etc. In the one or more activated positions, the optical fiber 138 can be nearer to an electrode or further away from an electrode as a result of an electrostatic force between them. For example, when an attractive electrostatic force exists between electrode 194 and the optical fiber 138, the distal portion 218 of the optical fiber 138 can move in direction 210. The distal end 180 of the optical fiber 138 can move correspondingly in direction 204. (In some embodiments, the distal end 180 can move in direction 206, as described below.)

It is understood that movement of optical fiber 138 includes the displacement of a part of the distal portion 218 of the optical fiber 138 relative to probe 190, handle 146, cannula 150, and/or optical element 152. For example, as shown in FIG. 6, attractive electrostatic forces between optical fiber 138 and electrode 194 can cause a part of distal portion 218 to bend towards electrode 194. Because a part of distal portion 218 bends towards electrode 194, the distal portion 218 is displaced relative to cannula 150 and/or optical element 152 such that the distal portion 218 has moved in the direction 210 towards electrode 194 and the distal end 180 has moved in the direction 204. In various embodiments, the part of distal portion 218 that bends towards electrode 194 and/or 196 can be between 0% and 50%, 10% and 40%, and 20% and 30% of the length 220 of distal portion 218. In various embodiments, the part of distal portion 218 that moves can be 50% and 100%, 60% and 90%, and 70% and 80% of the length 220 of distal portion 218. The part of distal portion 218 that bends can be more proximal than the part of distal portion 218 that moves.

A scanning process, during which the optical fiber 138 is oscillated with respect to optical element 152, can include multiple frequency cycles. For example, during a first half of a frequency cycle, for example, a positive voltage can be applied to optical fiber 138 such that optical fiber 138 acquires a positive charge (as shown in FIG. 6). A negative voltage can be applied to electrode 194 such that electrode 194 acquires a negative charge. The attractive electrostatic forces between electrode 194 and the optical fiber 138 can cause optical fiber 138 to move in direction 210 (e.g., towards electrode 194). Correspondingly, in some embodiments, the distal end 180 can move in direction 204 (e.g., as shown in FIG. 3).

In embodiments in which multiple electrodes are charged at the same time, a positive voltage can be applied to electrode 196 such that electrode 196 acquires a positive charge (as shown in FIG. 6), during the first half of the frequency cycle. The repulsive electrostatic forces between electrode 196 and the optical fiber 138 (which can be positively charged) can cause optical fiber 138 to move in direction 210 (e.g., towards electrode 194). Correspondingly, in some embodiments, the distal end 180 can move in direction 204 (as shown in FIG. 3).

For example, during a second half of the frequency cycle, a negative voltage can be applied to electrode 196 such that electrode 196 acquires a negative charge. The attractive electrostatic forces between electrode 196 and the optical fiber 138 (which can be positively charged) can cause optical fiber 138 to move in direction 208 (e.g., towards electrode 196). Correspondingly, in some embodiments, the distal end 180 can move in direction 206 (as shown in FIG. 4).

In embodiments in which multiple electrodes are charged at the same time, a positive voltage can be applied to electrode 194 such that electrode 194 acquires a positive charge, during the second half of the frequency cycle. The repulsive electrostatic forces between electrode 194 and the optical fiber 138 (which can be positively charged) can cause optical fiber 138 to move in direction 208 (e.g., towards electrode 196). Correspondingly, in some embodiments, the distal end 180 can move in direction 206 (as shown in FIG. 4).

The discussion above described oscillation of the optical fiber 138 by maintaining the charge of the optical fiber 138 and switching the charges of electrodes 194 and 196. In other embodiments, the charges of electrodes 194 and 196 can be maintained and the charge of the optical fiber 138 can be switched. In some embodiments, the charges of electrodes 194 and 196 are always opposite during a scanning process.

The voltages being applied to and/or the charges being acquired by optical fiber 138, electrode 194, and/or electrode 196 in the discussion herein are exemplary only. It is understood that negative voltage can be selectively applied to and a negative charge can be acquired by optical fiber 138, electrode 194, and/or electrode 196. Similarly, positive voltage can be selectively applied to and a positive charge can be acquired by optical fiber 138, electrode 194, and/or electrode 196. The various combinations of positive and negative charges acquired by optical fiber 138, electrode 194, and/or electrode 196 (and the subsequent generation of attractive and/or repulsive electrostatic forces) can be controlled by, e.g., controller 126 of imaging system 120 (FIG. 1).

In some embodiments, the distal portion 218 of optical fiber 138 maintains a linear profile during oscillation. For example, when the distal portion 218 of optical fiber 138 moves in direction 210, the distal end 180 can move in the same direction, e.g., direction 204. In other embodiments, as described herein, the distal portion 218 of optical fiber 138 is at least partially arcuately shaped during oscillation. For example, when the distal portion 218 of optical fiber 138 moves in direction 210, the distal end 180 can move in the opposite direction, e.g., direction 206. Such movement can occur, for example, when the distal portion 218 of the optical fiber 138 bends or deflects in the direction 210 because of an attractive electrostatic force between electrode 194 and optical fiber 138 that are charged with different polarities. The distal end 180, in response to the bending or deflection of the distal portion 218, can move in the direction 206 such that the optical fiber 138 is at least partially arcuately shaped. When a repulsive electrostatic force is generated between electrode 194 and optical fiber 138 and/or an attractive electrostatic force is generated between electrode 196 and optical fiber 138, optical fiber 138 can return towards its neutral position. The distal portion 218 of the optical fiber 138 can move in direction 208, and the distal end 180 of the optical fiber 138 can move in direction 204. Because of the repulsive electrostatic force generated between electrode 194 and optical fiber 138 and/or an attractive electrostatic force generated between electrode 196 and optical fiber 138, the optical fiber 138 can be moved past its neutral position. When this occurs, the distal portion 218 can bend or deflect in direction 208 and the distal end 180 can move in direction 204 such that the optical fiber 138 is at least partially arcuately shaped. In some embodiments, during a scanning process when optical fiber 138 is being oscillated, the distal portion 218 of the optical fiber 138 periodically switches between at least partial arcuate shapes that are mirror images of one another.

When one or more of electrode 194, electrode 196, and/or optical fiber 138 selectively acquire an electric charge causing attractive and/or repulsive electrostatic forces, the optical fiber 138 can be oscillated, as illustrated in FIGS. 3 and 4, and the imaging beam can be scanned across the target biological tissue, such as the retina. In some implementations, the actuator system 178 is configured to oscillate the distal end 180 of the optical fiber 138 within a frequency range between about 1 Hz and 100 Hz, between about 1 Hz and 50 Hz, between about 1 Hz and about 30 Hz, between about 5 Hz and 20 Hz, between about 10 Hz and 15 Hz, between about 1 Hz and 15 Hz, etc., although other frequency ranges, both larger and smaller, are contemplated. In some embodiments, electrode 194, electrode 196, and/or optical fiber 138 can have no charge for one-half of a frequency cycle and be charged for one-half of the frequency cycle. In other embodiments, electrode 194, electrode 196, and/or optical fiber 138 can have a charge with one polarity for one-half of the frequency cycle and a charge with the opposite polarity for one-half of the frequency cycle. The durations during which electrode 194, electrode 196, and/or optical fiber 138 is not charged, charged with one polarity, and/or charged with the opposite polarity can be greater than or less than one-half of the frequency cycle.

The positions of the distal end 180 of the optical fiber 138 depicted in FIGS. 3 and 4 can also be the neutral position for the actuator system 192. In that regard, the distal end 180 of the optical fiber 138 can begin in the position of FIG. 3 or FIG. 4 and then move to the position of FIG. 4 or FIG. 3, respectively, upon electrode 194, electrode 196, and/or optical fiber 138 being charged and electrostatic forces urging optical fiber 138 in direction 208 or 210. When the electrode 194, electrode 196, and/or optical fiber 138 are oppositely charged, optical fiber 138 moves towards the opposite direction 210 or 208.

In some embodiments, the actuator system 192 can include one or more restoring elements (e.g., coil spring, leaf spring, etc.) to facilitate returning the optical fiber 138 towards the starting, neutral position after electrostatic forces have caused movement of the optical fiber 138 in directions 208 and/or 210. The restoring element(s) can be mechanical and/or electromagnetic.

At least a portion of optical fiber 138 can have a reduced diameter compared to other parts of the same optical fiber and/or conventional optical fibers. For example, distal portion 218 of optical fiber 138 can have a reduced diameter. The distal portion 218 can include the extent of the optical fiber 138 that is being electrostatically actuated. The reduced diameter can be between 1% and 99%, 5% and 95%, 10% and 90%, 20% and 80%, 30% and 70%, 40% and 60%, etc., of the diameter of other parts of the same optical fiber and/or conventional optical fibers. For example, the reduced diameter can be in the range of 2 μm to 125 μm, 5 μm to 120 μm, etc. A smaller diameter results in a smaller cross-sectional area. An optical fiber with a smaller cross-sectional area can require less bending moment to cause the optical fiber to bend (e.g., when the distal portion of optical fiber 138 is acted on by an electrostatic force). In some embodiments, at least a portion of optical fiber 138 can be tapered (e.g., by an extruding process, etching, etc.). For example, the portion of the optical fiber 138 that has a reduced diameter may have been tapered. During fiber tapering, the geometry of the optical fiber can scale proportionally. For example, a 125 µm diameter fiber with a 5 µm diameter core is tapered by half, the result is a 62.5 µm diameter fiber with a 2.5 µm diameter core. In some embodiments, the diameter of the optical fiber 138 is reduced by etching the distal portion 218 such that the total diameter is reduced but the core diameter remains the same. For example, a 125 µm diameter fiber with a 5 µm diameter core can be etched so that the total diameter is reduced to 62.5 µm but the core diameter remains 5 µm.

The probe 190 can include stiffening member 212 positioned adjacent to optical fiber 138. Stiffening member 212 can be formed of a material that is more rigid than the optical fiber 138 such that the optical fiber 138 experiences a bending moment (e.g., as a result of its own weight) only in a portion distal to the distal end of stiffening member 212. Stiffening member 212 can be configured to add rigidity to a greater portion (compared to when no stiffening member 212 is provided in probe 190) of optical fiber 138 within an interior of optical fiber 138 such that optical fiber 138 is maintained in a neutral position coaxial with a longitudinal axis of cannula 150.

When the stiffening member 212 is included in probe 190, it can extend longitudinally along at least a portion of probe 190 and optical fiber 138. The stiffening member 212 can be disposed entirely in cannula 150 or housing 146, or portions of stiffening member 212 can be partially disposed in both cannula 150 and housing 146. In some embodiments, stiffening member 212 can be described as a stiffening tube that is disposed annularly around optical fiber 138. For example, stiffening member 212 can extend around an entirety of the perimeter of optical fiber 138. In other embodiments, stiffening member 212 can be described as a stiffening plate disposed adjacent to a portion of the optical fiber 138. Such a stiffening member can be linear, curved, or some combination thereof. The stiffening member 212 can be secured to the optical fiber 138 using a suitable adhesive (e.g., glue, epoxy, etc.), mechanical connection, and/or combinations thereof. Similarly, stiffening member 212 can be secured to the handle 146 using a suitable adhesive (e.g., glue, epoxy, etc.), mechanical connection, and/or combinations thereof.

When stiffening member 212 is provided in handle 146, the stiffening member 212 can be bent in a biasing direction to provide a compliant restoration force for optical fiber 138 (e.g., toward a neutral position when the optical fiber 138 is coaxial with a longitudinal axis of cannula 150). For example, the stiffening member 212 could be bent in the direction indicated by arrow 208 such that optical fiber 138 is biased towards the neutral position (e.g., in a direction opposite the direction 210 that optical fiber 138 is urged by attractive electrostatic forces between optical fiber 138 and electrode 194). The stiffening member 212 can be bent in addition to or in lieu of one or more restoring elements that are configured to return optical fiber 138 to a neutral position.

The discussion below generally refers to FIGS. 7, 8, and 9. FIG. 7 is a stylized illustration of a cross-sectional back view of an imaging probe along section line 8-8 of FIG. 5 in accordance with an aspect of the present disclosure. FIGS. 8 and 9 are stylized illustrations of a cross-sectional back view of an imaging probe, similar to that of FIG. 7, but showing multiple electrodes in accordance with an aspect of the present disclosure.

The illustrated embodiment of FIG. 7 includes two electrodes 232 and 242 within cannula 150. Electrodes 232 and 242 can be positioned or disposed annularly around optical fiber 222, symmetrically disposed around optical fiber 222, opposite one another, within two equally-divided halves of cannula 150, and/or 180° apart. The illustrated embodiment of FIG. 8 includes three electrodes 264, 274, and 284 within cannula 150. Electrodes 264, 274, and 284 can be positioned or disposed annularly around optical fiber 252, within equally-divided thirds of cannula 150, and/or 120° apart. The illustrated embodiment of FIG. 9 includes four electrodes 302, 312, 322, and 332. Electrodes 302, 312, 322, and 332 can be positioned or disposed annularly around optical fiber 292, symmetrically disposed around optical fiber 292, opposite at least one other electrode, within equally divided quadrants of cannula 150, and/or 90° apart.

It is understood that orientation and/or positioning of electrodes of FIGS. 7, 8, and 9 can vary in different embodiments. For example, electrodes 232 and 242 can be rotated 90° about optical fiber 222 such that electrodes 232 and 242 are positioned on the left and right of cannula 150 (compared to being positioned on a top and bottom of cannula 150 when cannula 150 is viewed from the perspective shown in FIG. 7). For example, two of electrodes 262, 272, and 282 can be positioned close to one another and farther away from the third electrode (compared to being positioned in equally-divided thirds as shown in FIG. 8).

The motion profiles discussed in the context of the actuator systems with two electrodes, as shown in, e.g., FIG. 7, generally focused on linear displacement of the optical fiber 138 within cannula, which can be utilized to produce a corresponding linear scan of the imaging beam across the target biological tissue. In other embodiments (as shown in, e.g., FIGS. 8 and 9), the actuator system includes three, four, or more electrodes that can be selectively activated, along with the optical fiber, to scan the optical fiber and the imaging beam across a two-dimensional scanning pattern. The two-dimensional scanning pattern can include a spiral, a raster, a constant-radius asterisk, a multiple-radius asterisk, a multiply folded path, other two-dimensional scan patterns, other patterns, and/or combinations thereof.

For example, a constant-radius asterisk scanning pattern can be achieved using the illustrated embodiment of FIG. 9. A controller, e.g., controller 126 of imaging system 120 (FIG. 1) can execute or cause the steps below to be executed. Electrode 262 and optical fiber 252 can be charged with opposite polarities such that an attractive electrostatic force is generated causing optical fiber 252 to move towards electrode 262. The same magnitude and polarity voltage can be applied to electrodes 272 and 282 such that they are charged the same as electrode 262, while electrode 262 remains charged. Optical fiber 252 experiences equal, attractive electrostatic forces in the directions of electrodes 262, 272, and 282, causing optical fiber 252 to move to the neutral position (e.g., coaxial with the longitudinal axis of cannula 150). Thus, first arm (e.g., in the direction of electrode 252) of the asterisk is scanned.

To scan the next arm (e.g., in the direction of electrode 272) of the asterisk, a voltage with the same polarity as the voltage applied to optical fiber 252 can be applied to electrodes 262 and 282 such that electrodes 262 and 282 acquire the same polarity charge as the optical fiber 252 and repulsive electrostatic forces are generated between optical fiber 252 and electrodes 262 and 282. The charge of optical fiber 252 is maintained (compared to the charge of optical fiber 252 during scanning of the first arm of the asterisk). The charge of electrode 272 is also maintained (compared to the charge of electrode 272 when all three electrodes were equally charged) such that an attractive electrostatic force continues to exist between optical fiber 252 and electrode 272. Because of the attractive electrostatic force between optical fiber 252 and electrode 272, and the repulsive electrostatic forces between optical fiber 252 and electrodes 262 and 282, optical fiber 252 can move towards electrode 272. The same magnitude and polarity voltage can be applied to electrodes 262 and 282 (compared to the voltage applied to electrode 272 all three electrodes were equally charged) such that they are charged the same as electrode 272, while the charge of electrode 272 is maintained. Optical fiber 252 experiences equal, attractive electrostatic forces in the directions of electrodes 262, 272, and 282, causing optical fiber 252 to move to the neutral position (e.g., coaxial with the longitudinal axis of cannula 150). Thus, the second arm (e.g., in the direction of electrode 262) of the asterisk is scanned.

To scan the last arm (e.g., in the direction of electrode 282) of the asterisk, a similar procedure as described with respect to scanning to the second arm of the asterisk can be repeated. A voltage with the same polarity as the voltage applied to optical fiber 252 can be applied to electrodes 262 and 272 such that electrodes 262 and 272 acquire the same polarity charge as the optical fiber 252 and repulsive electrostatic forces are generated between optical fiber 252 and electrodes 262 and 272. The charge of optical fiber 252 is maintained (compared to the charge of optical fiber 252 during scanning of the first arm of the asterisk). The charge of electrode 282 is also maintained (compared to the charge of electrode 282 when all three electrodes were equally charged) such that an attractive electrostatic force continues to exist between optical fiber 252 and electrode 282. Because of the attractive electrostatic force between optical fiber 252 and electrodes 282, and the repulsive electrostatic forces between optical fiber 252 and electrodes 262 and 272, optical fiber 252 can move towards electrodes 282. The same magnitude and polarity voltage can be applied to electrodes 262 and 272 (compared to the voltage applied to electrode 282 all three electrodes were equally charged) such that they are charged the same as electrode 282, while the charge of electrode 282 is maintained. Optical fiber 252 experiences equal, attractive electrostatic forces in the directions of electrodes 262, 272, and 282, causing optical fiber 252 to move to the neutral position (e.g., coaxial with the longitudinal axis of cannula 150). Thus, the third arm (e.g., in the direction of electrode 262) of the asterisk is scanned.

The two-dimensional scanning pattern described above is a non-limiting example. For example, one, two, three, four, five, or more arms of an asterisk pattern can be scanned. For example, the electrically conductive layer 224 and/or one or more of the electrodes 302, 312, 322, and 332 of FIG. 9 can be selectively charged and discharged such that the optical fiber 222 is moved to perform a raster scan. Other one-dimensional and/or two-dimensional scanning patterns can be implemented by the devices, systems, and methods described herein. In some embodiments, the optical fiber and/or the electrode(s) can be charged with discrete polarities. In some embodiments, an analog range of voltages can be applied to the optical fiber and/or the electrode(s) such that varying degrees of attractive and repulsive electrostatic forces are generated. Using analog voltages can provide a high resolution method scanning because of the analog range of partial attraction and/or repulsion between the optical fiber and/or the electrode(s).

Figure 10:
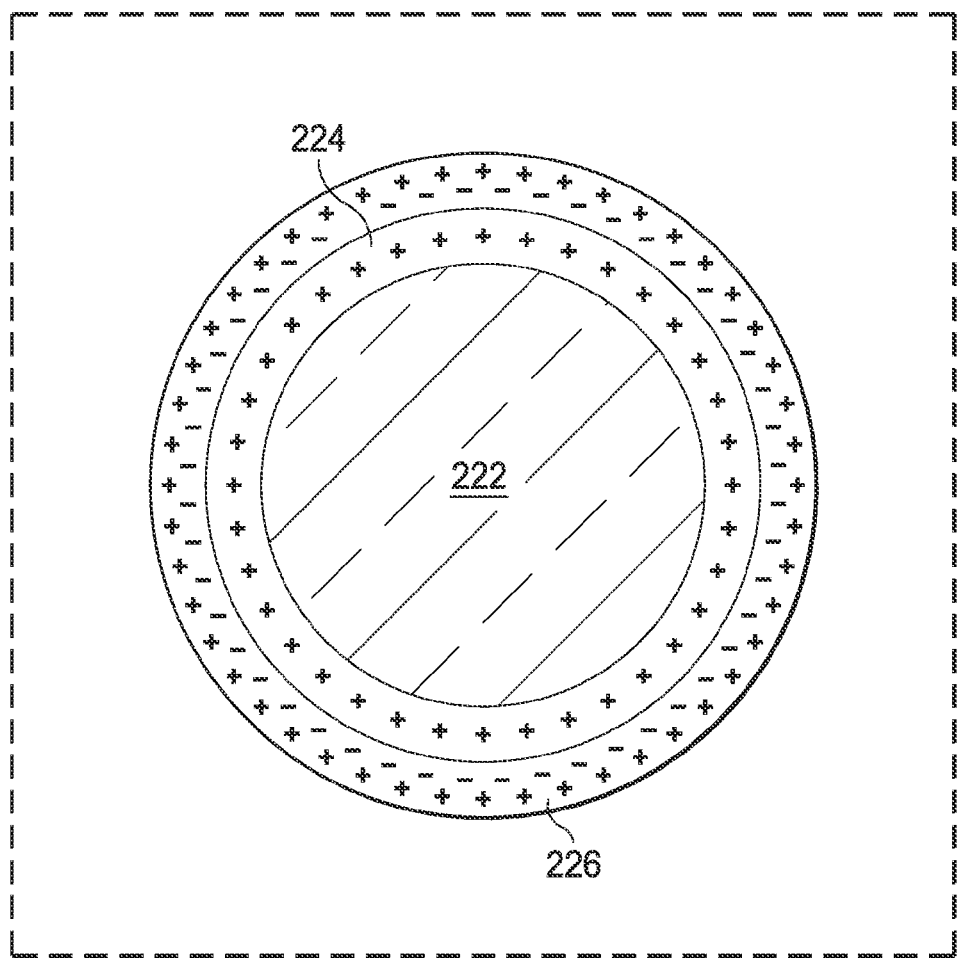
FIG. 10 is a stylized illustration of a cross-sectional back view of the optical fiber of FIG. 7 in accordance with an aspect of the present disclosure.

Optical fiber 222 is shown to include an electrically conductive layer 224. When a voltage is described herein as being applied to an optical fiber or an optical fiber is described herein as acquiring a charge, it is understood that the voltage is applied to the electrically conductive layer and the electrically conductive layer acquires the charge. In some embodiments, the optical fiber does not include an electrically conductive layer. In other embodiments, the optical fiber 222 includes the electrically conductive layer 224 and an insulating layer 226 (as shown in FIG. 10). The electrically conductive layer 224 can be disposed and/or positioned between the optical fiber 222 and the insulating layer 226.

Insulating layer 226 can be or can include a dielectric material. Dielectric materials are insulating by nature, and electric charges do not flow through them. Thus, they can serve the same purpose as solely an insulating coating (such as those described herein with respects to FIGS. 7, 8, and 9). Dielectric materials can also have one or more advantageous features. For example, dielectric materials can be polarized by an applied electric field. That is, the electric charges can shift from their equilibrium positions and can be aligned based on the applied electric field. For example, in the illustrated embodiment of FIG. 10, the electrically conductive layer 224 can acquire a positive charge. When insulating layer 226 is solely an insulating coating, the strength of the electric field associated with the charged electrically conductive layer 224 is decreased through the thickness of insulating layer 226. When insulating layer 226 is or includes a dielectric material, the portion (an interior- or optical fiber-facing portion) of the insulating layer 226 nearer to the positively-charged electrically conductive layer 224 is polarized and acquires an at least partial negative charge. The portion (an exterior- or cannula-facing portion) of the insulating layer farther from the positively-charged electrically conductive layer 224 is also polarized and acquires an at least partial positive charge. An exterior surface of the insulating layer 226 can have the same polarity charge as the electrically conductive layer 224. Thus, the electric field associated with electrically conductive layer 224 is carried through the insulating layer 226 and presented exteriorly (e.g., towards one or more electrodes). Such an arrangement can facilitate the oscillation of the optical fiber via electrostatic forces.

In a similar manner, one or more of the insulating layers associated with the electrodes of FIGS. 7, 8, and 9 can be or can include a dielectric material. For example, the interior- or optical fiber-facing insulating layers can be or can a dielectric material. An interior surface of the insulating layers can have the same polarity charge as the electrodes. Thus, the electrical field associated with the electrodes is carried through the insulating layers and presented interiorly (e.g., towards the optical fiber). Such an arrangement can facilitate the oscillation of the optical fiber via electrostatic forces.

Referring again to FIGS. 7, 8, and 9, exterior-facing surfaces (e.g., towards the cannula 150) of the electrodes are shown to include an insulating layer. For example, electrode 232 can include insulating layer 234 (FIG. 7), electrode 242 can include insulating layer 244 (FIG. 7), electrode 262 can include insulating layer 264 (FIG. 8), electrode 272 can include insulating layer 274 (FIG. 8), electrode 282 can include insulating layer 284 (FIG. 8), electrode 302 can include insulating layer 304 (FIG. 9), electrode 312 can include insulating layer 314 (FIG. 9), electrode 322 can include insulating layer 324 (FIG. 9), and/or electrode 332 can include insulating layer 334 (FIG. 9). Insulating layers on exterior facing surfaces of the electrodes can prevent undesired contact between the electrodes and cannula 150. Contact can result in voltage being applied to cannula 150. The application of a voltage to cannula 150 can be undesirable when the optical probe is at least partially disposed in a patient's eye. The insulating layer can be or can include an insulating coating. The insulating layer can be coupled to the optical fiber 138 using chemical processes; a suitable adhesive (e.g., glue, epoxy, etc.); mechanical connection; and/or combinations thereof. The insulating layer can be and/or can include a ceramic, polyethylene, polyvinyl chloride, polyimide, polymers, parylene, silicon dioxide, titanium dioxide, and/or other suitable insulating or dielectric material.

FIGS. 7, 8, and 9 show that interior-facing surfaces (e.g., towards the optical fiber 138) of the electrodes and/or an exterior surface of the optical fiber can include an insulating layer. For example, electrode 232 can include insulating layer 236 (FIG. 7), electrode 242 can include insulating layer 246 (FIG. 7), electrode 262 can include insulating layer 266 (FIG. 8), electrode 272 can include insulating layer 276 (FIG. 8), electrode 282 can include insulating layer 286 (FIG. 8), electrode 302 can include insulating layer 306 (FIG. 9), electrode 312 can include insulating layer 316 (FIG. 9), electrode 322 can include insulating layer 326 (FIG. 9), and/or electrode 332 can include insulating layer 336 (FIG. 9). At least a portion (e.g., the entirety of optical fiber 138 in an interior of probe 190, the distal portion 218 of the optical fiber 138, the portion of the optical fiber 138 that includes an electrically conductive layer) of optical fiber 138 can include an insulating layer. For example, optical fiber 222 can include insulating layer 226. Insulating layers on interior-facing surfaces of the electrodes and/or an exterior surface of the optical fiber can be configured to prevent electrical communication between the electrodes and the electrically conductive layer of the optical fiber. Insulating layers can prevent undesired electric discharge when the optical fiber contacts one or more electrodes. Electric discharge can result in the electrostatic forces that existed between the optical fiber and one or more electrodes being extinguished. Electric discharge can also cause sparking. Contact between the optical fiber and one or more electrodes can occur during actuation of the optical fiber as the optical fiber is electrostatically attracted toward one or more electrodes. For example, if an exterior surface of the optical fiber includes an electrically conductive layer that contacts an electrically conductive electrode, an electric discharge can occur. Such electric discharge can be undesirable when the optical probe is at least partially disposed in a patient's eye. The insulating layer can be or can include an insulating coating. The insulating layer can be coupled to the optical fiber 138 using chemical processes; a suitable adhesive (e.g., glue, epoxy, etc.); mechanical connection; and/or combinations thereof. The insulating layer can be and/or can include a ceramic, polyethylene, polyvinyl chloride, polyimide, polymers, parylene, silicon dioxide, titanium dioxide, and/or other suitable insulating or dielectric material.

It is understood that, when an electrode and/or optical fiber is described as including an insulating layer, the insulating layer can be a component distinct from the optical fiber itself, such as a coating, sleeve, etc., that is applied and/or otherwise coupled to the optical fiber. In some embodiments, one or more of the insulating layers of the electrodes and/or the optical fiber can include a dielectric material, as described in more detail with respect to the FIG. 10. In some embodiments, the exterior-facing and interior-facing insulating layers of the electrodes and/or optical fiber can be or can include the same materials. In others embodiments, the exterior-facing and interior-facing insulating layers can be or can include different materials. For example, the interior-facing insulating layers can be or can include a dielectric material while the exterior-facing insulating layers are not or do not include a dielectric material.

Embodiments as described herein can provide an imaging probe having an actuator that utilizes at least one charged electrode to impart motion to an optical fiber positioned within an imaging probe by an electrostatic force. The examples provided above are exemplary only and are not intended to be limiting. One skilled in the art can readily devise other systems consistent with the disclosed embodiments which are intended to be within the scope of this disclosure. As such, the application is limited only by the following claims.

The invention claimed is:

1. An ophthalmic imaging probe, comprising:
a handle;
a cannula coupled to the handle;
an optical fiber positioned at least partially within the handle and the cannula, the optical fiber configured to receive an imaging light from an imaging light source and guide the imaging light to an optical element positioned within the distal portion of the cannula; and
an actuator system configured to impart motion to the optical fiber, the actuator system comprising:
a plurality of electrodes positioned within the cannula, each electrode configured to impart motion to the optical fiber by selectively imparting an electric charge to at least one of the electrode and the electrically conductive layer of the optical fiber, each electrode extending longitudinally along the cannula, each electrode following the shape of the cannula and extending in a curved manner around a portion of an interior perimeter of the cannula.

2. The probe of claim 1, wherein:
each electrode extends along at least one third (⅓) of a longitudinal extent of the cannula.

3. The probe of claim 1, wherein:
a first electrode and a second electrode are symmetrically disposed around the optical fiber.

4. The probe of claim 1, wherein:
the actuator system is configured to impart motion to the optical fiber to scan the imaging light over a two-dimensional scanning pattern.

5. The probe of claim 4, wherein:
the two dimensional scanning pattern comprises at least one of a spiral, a raster, a constant-radius asterisk pattern, a multiple-radius asterisk pattern, and a multiply folded path.

6. The probe of claim 1, wherein:
the optical fiber includes an electrically conductive layer.

7. The probe of claim 6, wherein:
the optical fiber includes an insulating layer.

8. The probe of claim 7, wherein:
the electrically conductive layer is disposed between the optical fiber and the insulating layer.

9. The probe of claim 7, wherein:
the insulating layer comprises a dielectric material.

10. The probe of claim 1, wherein:
an interior-facing surface of at least one electrode includes an insulating layer.

11. The probe of claim 1, wherein:
an exterior-facing surface of at least one electrode includes an insulating layer.

12. The probe of claim 1, wherein:
a proximal section of the optical fiber is fixedly secured to a proximal portion of the handle.

13. The probe of claim 1, wherein:
at least one electrode is fixedly secured to the cannula.

14. The probe of claim 1, wherein:
the optical element comprises a gradient index (GRIN) lens.

15. The probe of claim 1, wherein:
the optical element is mechanically coupled to a distal end of the optical fiber so that the optical element moves with the distal end of the optical fiber.

16. The probe of claim 1, wherein:
the actuation system is configured to impart motion to the optical fiber to scan the imaging light along a scanning pattern with a linear extent at a target biological tissue between 1 mm and 5 mm at a distance between 5 mm and 10 mm from a distal end of the cannula.

17. An ophthalmic imaging system, comprising:
an imaging light source configured to generate an imaging light;
an optical guide in optical communication with the imaging light source, the optical guide configured to receive the generated imaging light from the imaging light source; and
a probe in optical communication with the optical guide, the probe comprising:
  a handle;
  a cannula coupled to the handle;
  an optical fiber positioned at least partially within the handle and the cannula, the optical fiber including an electrically conductive layer, wherein the optical fiber is configured to receive the imaging light from the optical guide and guide the imaging light to an optical element positioned within the distal portion of the cannula; and
  an actuator system configured to impart motion to the optical fiber, the actuator system including a plurality of electrodes positioned within the cannula, each electrode configured to impart motion to the optical fiber by selectively imparting an electric charge to at least one of the electrode and the electrically conductive layer of the optical fiber, each electrode extending longitudinally along the cannula, each electrode following the shape of the cannula and extending in a curved manner around a portion of an interior perimeter of the cannula.

18. The ophthalmic imaging system of claim 17, further comprising:
a controller in communication with the light source, the controller configured to control actuation of the imaging light source for an optical coherence tomography (OCT) imaging procedure.

19. The ophthalmic imaging system of claim 18, wherein:
the controller is further configured to process data obtained by the probe and output imaging data to a display in communication with the controller.

20. The ophthalmic imaging system of claim 18, wherein:
the controller is further configured to selectively cause a voltage to be applied to at least one of the electrically conductive layer of the optical fiber and each electrode such that at least one of the electrically conductive layer of the optical fiber and each electrode acquires an electric charge.

* * * * *